United States Patent
Kojovic et al.

(10) Patent No.: US 8,272,247 B2
(45) Date of Patent: Sep. 25, 2012

(54) APPARATUS FOR DETERMINING BREAKAGE PROPERTIES OF PARTICULATE MATERIAL

(75) Inventors: Toni Kojovic, Sinnamon Park (AU); Stephen Larbi-Bram, Indooroopilly (AU); Fengnian Shi, Forest Lake (AU); Emmanuel Manlapig, Chapel Hill (AU)

(73) Assignee: The University of Queensland, St. Lucia (AU)

( * ) Notice: Subject to any disclaimer, the term of this patent is extended or adjusted under 35 U.S.C. 154(b) by 749 days.

(21) Appl. No.: 12/301,299

(22) PCT Filed: May 10, 2007

(86) PCT No.: PCT/AU2007/000631
§ 371 (c)(1),
(2), (4) Date: Feb. 11, 2009

(87) PCT Pub. No.: WO2007/134367
PCT Pub. Date: Nov. 29, 2007

(65) Prior Publication Data
US 2009/0199625 A1    Aug. 13, 2009

(30) Foreign Application Priority Data

May 18, 2006 (AU) ................................ 2006902688
Aug. 15, 2006 (AU) ................................ 2006904417

(51) Int. Cl.
*G01N 3/31* (2006.01)
(52) U.S. Cl. ...................... 73/12.11; 73/12.05; 73/865.3
(58) Field of Classification Search .................. 73/12.05, 73/12.11, 865.3
See application file for complete search history.

(56) References Cited

U.S. PATENT DOCUMENTS

| | | | |
|---|---|---|---|
| 3,224,685 A * | 12/1965 | Brack et al. ........................ 241/5 |
| 3,675,373 A * | 7/1972 | Putnam ............................ 451/38 |
| 3,716,196 A | 2/1973 | Motek et al. |
| 4,002,301 A | 1/1977 | Shurtleff |

(Continued)

FOREIGN PATENT DOCUMENTS

DE    3905365 A1    11/1989

(Continued)

OTHER PUBLICATIONS

PCT International Search Report for PCT/AU2007/000631 dated Jun. 27, 2007.

(Continued)

*Primary Examiner* — Hezron E Williams
*Assistant Examiner* — Paul West
(74) *Attorney, Agent, or Firm* — Sutherland Asbill & Brennan LLP

(57) ABSTRACT

An apparatus for determining the breakage properties of a particulate material, the apparatus including: a support; a rotor mounted relative to the support and including at least one guide channel through which a particle of the particulate material is guided in use, the guide channel having an inlet and an outlet; a drive associated with the rotor; a feed channel for feeding particles of the particulate material to the inlet of the guide channel; a stator associated with the rotor and including an impact surface that is radially spaced from a circumferential edge of the rotor; and a collector for collecting pieces of the particulate material following impact; wherein the apparatus is provided with a control system for accurate control and adjustment of impact velocity of the particulate material with the impact surface.

44 Claims, 5 Drawing Sheets

U.S. PATENT DOCUMENTS

| | | | | |
|---|---|---|---|---|
| 4,138,067 A | * | 2/1979 | Planiol | 241/275 |
| 5,009,371 A | * | 4/1991 | Nickel | 241/187 |
| 5,125,585 A | | 6/1992 | Williams | |
| 5,275,631 A | | 1/1994 | Brown et al. | |
| 5,482,218 A | | 1/1996 | Ha | |
| 2004/0113002 A1 | * | 6/2004 | Tessier et al. | 241/275 |
| 2005/0034832 A1 | * | 2/2005 | Sparks et al. | 164/5 |

FOREIGN PATENT DOCUMENTS

| | | |
|---|---|---|
| EP | 0425781 B1 | 5/1991 |
| EP | 0 702 598 B1 | 2/1997 |
| JP | 2004-277709 A | 10/2004 |
| SU | 926565 | 5/1982 |
| SU | 1658018 A1 | 6/1991 |
| WO | WO 00/10709 A1 | 3/2000 |
| WO | 2004/020103 A1 | 3/2004 |

OTHER PUBLICATIONS

Office Action issued by the Eurasian Patent Office on Jan. 14, 2010.

Napier-Munn et al., "Mineral Comminution Circuits: Their Operation and Optimisation," Julius Kruttschnitt Mineral Research Centre, 1996, pp. 71-78.

Supplementary European Search Report for EP Application No. 07 71 8878 dated Mar. 2, 2010 (2 pages).

* cited by examiner

APPARATUS FOR DETERMINING BREAKAGE PROPERTIES OF PARTICULATE MATERIAL

CROSS REFERENCE TO RELATED APPLICATIONS

This application claims the priority benefit of PCT/AU2007/000631 filed on May 10, 2007 and Australian Application Nos. 2006902688 and 2006904417 filed May 18, 2006 and Aug. 15, 2006, respectively.

FIELD OF THE INVENTION

This invention relates to apparatus for determining the breakage properties of a particulate material. This invention also extends to a method for determining the breakage properties of a particulate material. Further, the invention extends to a method for determining the probability of breakage of a particulate material.

This invention relates particularly but not exclusively to apparatus for quickly and efficiently determining the breakage characteristics or properties of test particles of a material, for example coal and mineral ore particles, both in a laboratory setting and also in a full scale mineral processing plant. It will therefore be convenient to hereinafter describe the invention with reference to this example application. However, it is to be clearly understood that the invention is capable of broader application. It is not to be limited to mineral processing applications.

BACKGROUND TO THE INVENTION

Generally, mineral bodies are blasted with explosives to break up the host rock and enable the broken rock pieces to be removed from the rock body. Blasting with explosives will break up the rock body in a rather crude fashion. The broken rock pieces will generally have a large size distribution with some large pieces of rock and also some small pieces of rock.

While this enables the rock pieces to be physically removed from the host body of rock, further work needs to be done on reducing the size of the rock pieces before they are sent to a beneficiating plant for the recovery of value particles from gangue or waste particles.

The general reduction in the size of particles after blasting is known as comminution and is carried out in crushers and mills. As discussed above, the size of the rock particles needs to be reduced for the subsequent beneficiation process. In particular, the number of large particles from the blasting step should be reduced to as low a level as possible to liberate the valuable mineral in the beneficiation process. It is also desirable to narrow the size distribution of particles that are fed into the beneficiation process, again for liberation of valuable mineral in the subsequent beneficiation process.

The comminution of particles to effect a reduction in particle size is carried out in crushers and mills. Mills may comprise ball or rod mills as well as semi-autogenous grinding (SAG) mills and autogenous grinding (AG) mills.

As a general proposition, mills in the mineral processing industry operate with a low level of efficiency. By this is meant the conversion of input energy, for example electrical energy, into energy that actually breaks the particles is very low. Often the mills are operated crudely based on an operator's understanding of the mill and there is very little science in the operation of the plant. Further the mill settings during operation of the mill are often not adjusted depending on the characteristics of the particles being processed by the mill at any one time.

However, it is well recognised that particle breakage properties for different ore bodies and types of rocks vary greatly. The characterization of particle breakage needs to be better understood and determined. This characterisation of particle breakage can then be used to achieve a greater efficiency in the breakage of particles in a mill.

Clearly, therefore, it would be advantageous if the mill operation could be fine tuned during operation to take into account these differences in particle breakage properties. This would then open up the possibility of more efficient usage of the mills with an improved rate of conversion of input energy to particle breakage within the mill.

The Applicant has developed a prior art test for characterising the breakage of particles that is based on a certain impact energy.

This test is known as the drop weight test and is carried out on laboratory scale equipment in a laboratory to provide some insight into the breakage of particles when subjected to an impact force.

Typically a mine operator sends an ore through to a tester who then conducts the drop weight test on the ore sample for a number of different size fractions. The test results show a size distribution of broken particles for each of the size fractions tested for a certain impact or collision energy.

The test results enable a user to characterise their ores for the design of a mill. This can then be used as an input in the modelling of a mill process, or to assist in optimisation of a given mill or to make changes to the mill settings.

This apparatus, an example of which is illustrated in FIG. 1, comprises a vertical frame 2 extending up from a solid base 3. An impact weight 4 is guided by means of guide rails between an upper position above the base and a lower position in which it collides with a particle 5 that is placed on the base.

In use, a particle to be tested is placed on the base beneath the weight. The weight is lifted up to a certain height and then released allowing it to fall under the influence of gravity. At the bottom of the guide the weight collides with the test particle causing it to break. The broken particles are then recovered and their size distribution can be analysed.

The impact energy that is applied to the particles may be varied. For example, the weight that is placed on the frame may be varied. Further the height from which the weight is dropped can be varied. This enables the breakage properties of a given fraction of particles to be studied for collisions with different input energies or impact forces.

The test described above can be repeated for a number of test particles from the same fraction providing information on how the particle breaks when subjected to that impact energy. It is important that a sufficiently large sample of particles be tested to give statistical validity to the characterisation of particle breakage. Obviously, the greater the number of particles that are tested the better the statistical validity of the results.

Over a number of samples of the same size fraction the results will tend to show how a particle will break for a given impact energy. For example, the particle may break into relatively few particles of about the same size. Alternatively, it may break into many small particles and a few large particles.

A further example apparatus for testing particle breakage properties is shown in FIG. 2.

Basically, the apparatus comprises a frame 6 mounted on a base 7 and extending up therefrom. A rebound pendulum 8 with a block towards its lower end is centrally mounted below the frame in a fixed position and does not move. A rock particle 9 to be tested is mounted in a fixed position on the rebound pendulum.

A swinging impact pendulum is also mounted from the frame and swings like a pendulum below the frame. The impact pendulum is sized and positioned to collide with the rebound pendulum, and specifically the test particle mounted on the rebound pendulum. A collection box for collecting the broken particles from the test particle is positioned below the rebound pendulum.

In use, a rock particle to be tested is positioned on an impact face of the rebound pendulum. An impact pendulum of set weight is lifted up to a set height and then released so that it swings down and then collides with the rebound pendulum. The sample rock on the collision surface of the rebound pendulum is struck by the impact pendulum. This collision causes particle breakage. The broken particles fall into the collection box from where they can be collected and analysed. Typically the particle size distribution of the broken particles is determined using classification screens.

The apparatuses described above with reference to FIGS. 1 and 2 have some limitations.

A first major limitation is that the tests are conducted manually. For each test involving collision with a particle, the particle needs to be placed on the support manually and the weight needs to be lifted and dropped. The broken particles then need to be manually recovered and placed in a sample container for further analysis. The particle size distribution needs to be determined manually using a size classification apparatus.

The process is not automated at all and carrying out tests is very time consuming. Generally, the tests are carried out by a laboratory technician and the labour cost alone of carrying out the tests is substantial.

Further, it will be readily apparent to the skilled addressee that a large number of tests need to be conducted for each size fraction of particle to confer some statistical validity to the results. Generally, 10 to 30 particles of each size fraction need to be subjected to the same test and the results of these tests analysed collectively. However, if only 10 to 30 samples of each particle size are tested the sample size is sub-optimum. This impacts on the statistical validity of the results and the consequent accuracy of the results. From a statistical point of view it would be advantageous if a substantially greater number of particles could be tested for each size fraction, for example testing a sample of 40 to 100 particles per size fraction, or 50 to 70 particles.

A further limitation of the drop weight test described above is that the smallest size of particle that can realistically and practically be tested by the apparatus is 10 mm in diameter. It is very difficult and time consuming to try and mount a particle that is smaller than this on the rebound pendulum. The problem with this is that a sizeable percentage of the particles that are fed into the mill in an operating plant are less than 10 mm in diameter. Thus existing test procedures do not test particles of less than 10 mm and do not provide any insight into their breakage characteristics. By implication, the test results assume that these particles break in the same way as particles that are greater than 10 mm. However, experiments conducted by the Applicant suggest that this assumption is not valid and particles that are less than 10 mm often break differently to the larger particles.

The drop weight tester has a further limitation that will be described below. The Applicant's investigations into the modes of particle breakage within a mill show that there are two types of breakage within a mill. Firstly, there are high energy impacts. Secondly, there is breakage due to repeated small energy impacts. Recent research on the impact energy distribution pattern in an autogenous mill operation has shown that small energy impacts take place at a much higher frequency than high energy impacts. Accordingly, it would be extremely beneficial if a particle breakage tester was capable of characterising particle breakage due to repeated small energy impacts.

When the drop weight tester is used to test particles using impacts at very low specific energy levels, some particles will require as high as 100 repeated hits before they eventually break. This procedure is very time-consuming and labour-extensive to quantify with the drop weight tester. As a compromise, a reduced number of particles could conceivably be used for the incremental breakage test. However, the reduced number of test particles will affect the statistical validity of the test results.

Clearly, therefore, it would be advantageous if an apparatus for testing the breakage characteristics of a particulate material could be devised that ameliorated at least some of these shortcomings.

SUMMARY OF THE INVENTION

According to one aspect of this invention there is provided an apparatus for determining the breakage properties of a particulate material, the apparatus including:

a support;

a rotor mounted relative to the support and including at least one guide channel through which a particle of the particulate material is guided in use, the guide channel having an inlet and an outlet;

a drive associated with the rotor;

a feed channel for feeding particles of the particulate material to the inlet of the guide channel;

a stator associated with the rotor and including an impact surface that is radially spaced from a circumferential edge of the rotor; and a collector for collecting pieces of the particulate material following impact;

wherein the apparatus is provided with a control system for accurate control and adjustment of impact velocity of the particulate material with the impact surface.

The support may take any suitable form. Preferably the support comprises a base for mounting or positioning the apparatus on a support surface, such as the floor, and a frame extending up from the base. The frame may have upright members extending up from the base on at least two opposed sides of the base.

The rotor may also take any suitable form. Preferably the rotor comprises a flattened, substantially circular body having two major surfaces. Preferably, the rotor is oriented with its major surfaces extending in a substantially horizontal plane and the rotor rotates about a substantially vertical axis.

The rotor includes at least one guide channel. If the rotor is a solid, flat mass the guide channel is preferably defined by a channel that extends radially within the solid mass from a substantially central position to the circumferential edge of the rotor. In that case, the distal end of the channel defines the outlet of the guide channel. The inlet of the guide channel may be formed by an opening in one of the major surfaces of the rotor, the opening being associated with the channel. Preferably the inlet is at or proximate to the central position of the rotor. The, or each, channel guides the particles along a linear path in a radially outward direction when the particles are under the influence of centrifugal force caused by rotation of the rotor.

In a preferred embodiment, the rotor includes a plurality of guide channels, for example a plurality of channels extending within the solid mass of the rotor from a common central position to the circumferential edge of the rotor. The rotor may define for example 2 to 6 channels, preferably 3-5 channels, more preferably 4 channels. Preferably the channels are circumferentially spaced from each other, more preferably equidistantly circumferentially spaced from each other.

In one form the rotor includes four channels that have a common inlet positioned in the centre of the rotor and that extend substantially perpendicularly to each other. Each channel extends linearly from the centre of the rotor to an outlet positioned on the circumferential edge of the rotor.

As noted above, the rotor may be formed from a block of material, for example steel, and the channels may be machined into the block. The channels may also be formed by sections of pipe or conduit mounted on the rotor and radiating out from the centre thereof.

The channels are preferably at least 20 mm in diameter, and may be about 30 mm in diameter. Applicant has found that channels of this size work well and do not suffer from blockages, although other sizes could be used. In particular, it has also been found that channels of up to about 70 mm or more may be useful for larger particles.

The drive may include any suitable means for supplying rotational drive to the rotor. In one embodiment, the drive includes an electric motor and a drive transmission that is coupled to the motor and the rotor to transmit drive from the motor to the rotor. The drive transmission may further include a belt drive, for example with drive pulleys coupled to the motor and the rotor for transferring drive from a gearbox to the rotor.

The rotor may ultimately be mounted on the support. A bearing may be interposed between an upper formation associated with the rotor and a lower formation associated with the support. Advantageously, this supports the rotor in its vertical position while permitting it to rotate.

The control system may take any suitable form. Importantly, the control system must be able to accurately and adjustably control the impact velocity of the particulate material with the impact surface. As will be discussed in more detail below, this is distinguished from the control of the circumferential speed of the rotor on the presumption that the impact may be calculated therefrom by theory. Preferably, the control system controls the impact velocity of the particulate material within a relative difference of less than 2%, preferably regardless of ore type, particle size and particle shape.

As will be considered in detail below, the control system preferably includes a processing unit for receiving an input of the circumferential speed of the rotor and correlating this with the actual impact velocity of a particle emitted from the guide channel of the rotor.

The control of the impact velocity may be achieved by any suitable means. Preferably the control system, through the drive, includes means for controlling the circumferential or rotational speed of the rotor, most preferably with a high degree of accuracy. It will be appreciated that the speed of the rotor determines the amount of energy imparted to the particle. The control system also preferably provides a means for adjusting, preferably finely adjusting, the rotational speed of the rotor. This may be achieved by adjusting the amount of current supplied to the coil of the motor, for example through a variable frequency inverter, when the drive is an electric motor. This enables the rotor to be set at different speeds corresponding to different energy levels that may be imparted to test particles of the particulate material in use.

When included, the variable frequency inverter enables the level of current being supplied to the motor to be increased causing the rotor to speed up. It also enables the current to the motor to be reduced which will have the opposite effect. Alternatively, a potentiometer may be used to rotate the rotor at different speeds with a high degree of accuracy.

An important feature of the apparatus is the inclusion of a control system, generally for managing the drive, to cause the rotor to rotate at a very precise speed and to be able to correlate that speed with the actual impact velocity of the particulate material accurately. This then enables the amount of kinetic energy imparted to successive particles undergoing the same test to be substantially the same, preferably exactly the same, for the results to have validity and benefit. The kinetic energy of the particles when they collide with the impact surface has an effect on how they break. Put another way, the breakage properties of a particulate material are functionally dependent on impact energy.

The control system may also include means for measuring the speed of rotation of the rotor. For example, this may include an optical or mechanical tachometer. As mentioned above, it is useful if the control system measures the speed of the rotor accurately because the input speed determines the input energy imparted to the particle being tested.

The tachometer for accurately measuring the speed of the rotor may be important as over time the ability of the inverter to accurately control the speed of the rotor may drop off. In such a case the tachometer provides accurate information to the control system of the actual speed of the rotor.

The feed channel may take any suitable form, but preferably includes a feed channel having an inlet and an opposed outlet through which particles to be tested can pass, generally in sequence and in turn. Thus, a preferred feature of the feed channel is that the particles to be tested pass through it one at a time and this way are fed to the rotor one at a time.

The feed channel may extend substantially vertically with its inlet at the upper end and the outlet end at the lower end. The outlet is preferably positioned above a common inlet to the guide channels of the rotor, for example the outlet may be spaced a short distance above the inlet to the guide channels substantially in the centre of the rotor.

The feed channel may have a flared inlet, for example resembling a funnel, for facilitating feeding of particles through the inlet. Further, the feed channel may be mounted on the frame extending up from the base.

The feed channel may be associated with a particle storage device, for example a storage hopper that is positioned above the inlet to the feed channel, containing a supply of particles to be tested. Preferably the particle storage device, for example the hopper, has an outlet that is sized to limit the flow of particles through the outlet.

The feed channel may further be associated with an intermediate conveying device for conveying particles from the outlet of the hopper to the inlet of the feed channel. The intermediate conveying device may be a vibrating feeder, for example a vibrating conveyor belt.

The intermediate conveying device may feed the particles one at a time from the outlet of the hopper into the inlet of the feed channel. The conveying device effectively jogs the particles out of the hopper, along a conveying belt and into the feed channel.

The stator defining the impact surface may comprise a body, for example a fixed body in the form of an anvil, that extends circumferentially around the rotor and that is spaced outwardly from the circumferential edge thereof. The rotor and stator are preferably mounted on the frame of the support.

Thus, the stator may fully surround the rotor and be at substantially the same height as the rotor.

In one form, the impact surface is configured such that particles discharged from the guide channels of the rotor impact it at an angle of 70 degrees to 100 degrees, for example 80 degrees to 98 degrees, for example at a substantially perpendicular angle of impact.

In use, particles fed to the apparatus are ejected from the guide channel(s) and collide with the impact surface of the stator at an angle that is close to 90 degrees to the surface. Accordingly, most of the kinetic energy of the particle striking the impact surface is directed to particle breakage. If the particle glances off the impact surface at an angle, part of the energy is retained by the particle as kinetic energy, and is not directed into breakage of the particle.

The impact surface may include a plurality of discrete surface segments arranged stepwise relative to each other extending around the impact surface. If so, advantageously each of these segments will receive particles being discharged from the rotor at substantially ninety degrees. Further, each of the surface segments may be curved slightly. Again the curve on the surface segments of the impact surface may be designed so that the particles emitted from the rotor strike the impact surface at as close to ninety degrees as possible. The impact surface with its discrete segments may collectively have a saw tooth configuration when viewed in plan view.

In another form the impact surface may be configured such that the particles discharged from the guide channels of the rotor impact with a glancing blow, for example at 20 degrees to 70 degrees, for example at 30 degrees to 60 degrees to the impact surface. This tests the breakage of the particles when exposed to shear type forces.

Another option would be to use the same impact surface as that described above for the substantially perpendicular impact, that is the saw tooth shaped impact surface, and vary the speed of the rotor such that the particles issuing from the rotor strike the impact surface at lower energy levels to test the incremental breakage of the particles.

It is advantageous if the apparatus actually mimics the different mechanisms of breakage of particles within a mill. Some of the breakage is due to direct impact. However, other breakage is due to shear type impacts where the particle strikes another particle or a ball or the lining of the mill with a glancing blow. The glancing tests described above enable the breakage characteristics of the shear type impacts to be determined. Applicant is aware that different particles can show markedly different behaviour for direct impact and shear impact.

In order to ensure that the stator is easily accessible for cleaning, thereby advantageously reducing the effects of cross contamination and sample loss between tests, the stator is preferably easily accessible. For example, in one embodiment the stator is included in a lid adapted to enclose the rotor. Preferably, the lid is mechanized.

The stator, which may take the form of an anvil body, may include a lining providing a wear surface that assumes wear resulting from the impact of particles discharging from the rotor. The lining may comprise a plurality of removable wear plates that can be removably attached to the stator and which can be removed and replaced with fresh wear plates as and when required. The wear plates may be made of steel or other suitable material. Preferably the wear plates are made from steel toughened by a heat treatment.

The apparatus may further include a housing within which the rotor and the stator are housed. The housing may be sealed so that the air pressure within the housing can be reduced to below atmospheric pressure. This enables a vacuum to be applied to the annular space between the rotor and the impact surface of the stator during testing.

By testing particle breakage in a vacuum the influence of drag and air resistance on small particles can be reduced or even removed. This enables more accurate test results to be obtained for small particles.

The collector for collecting the broken pieces of particle after impact preferably includes a collection chute positioned beneath the rotor and stator. The collection chute may be substantially conical and may taper in from a diameter greater than the diameter of the impact surface to a narrow diameter of a few centimeters, for example 20-50 mm. This then feeds the broken particles very specifically into a single location.

The apparatus may further include a classifier for classifying the broken particles into different size groups, preferably for automatically classifying the particles.

The classifier may comprise at least one classification screen that separates the broken particles into one fraction that is above a predetermined size and another fraction that is below the predetermined size. In one embodiment the classifier includes a single screen that is used to determine the $T_{10}$ product fineness index as a result of the particle breakage. That is, the weight percentage of broken particles passing through a screen having openings that are $1/10^{th}$ of the mean size of the feed particles.

It should be appreciated that the classifier may also comprise a plurality of classification screens. Such an arrangement could classify the broken particles into several size fractions, for example 4 to 8 size fractions. This more detailed classification can then be used to provide more comprehensive insight into the PSD of the broken particles for any size fraction of feed particles.

In alternative embodiments, the classifier is a non-mechanical classifier. For example, the classifier may be an optical classifier that advantageously enables quick and easy analysis of the particle size distribution of the broken particles by feeding them into the optical classifier. In this case, the analysis may be easily imaged onto a screen using appropriate software and considered, or saved for future reference.

The collector may also include means for weighing, for example automatically weighing, the different size fractions of broken particles.

This invention also extends to a method of determining breakage properties of a particulate material including the steps of:

feeding a plurality of discrete particles of the particulate material to the apparatus in accordance with the invention described above;

analysing resultant broken pieces of the discrete particles following impact in the apparatus; and correlating the resultant broken pieces with breakage properties of the particulate material.

The apparatus used in the method may include any one or more of the optional or preferred features of the apparatus described above.

The method may include dividing the particles of particulate material up into a plurality of size fractions and then testing each of the size fractions in turn in the apparatus described above.

The step of dividing up the particulate material into size fractions preferably includes dividing it up into narrow size fractions.

According to another aspect of the invention there is provided a method for determining breakage properties of a particulate material, the method comprising the steps of:

imparting an amount of kinetic energy to at least one particle of the particulate material;

causing the particle possessing said amount of kinetic energy to impact against an impact surface at a predetermined impact velocity and break;

analysing resultant broken pieces of the particle following impact; and correlating the resultant broken pieces with breakage properties of the particulate material.

The step of imparting an amount of kinetic energy to the particle may be achieved by any suitable means. However, the amount of energy imparted to the particle must be precise in order to ensure that the predetermined impact velocity of the particle is achieved. The kinetic energy may be applied to the particle by feeding the particle into a guide channel, for example as provided in the apparatus described above in accordance with the earlier aspect of the invention, and displacing the particle along the guide channel. It is reiterated that the predetermined impact velocity is the actual impact velocity of the particle and is not the presumed impact velocity that may be calculated in light of the circumferential speed of a rotor of an apparatus as described above.

In order to obtain statistically relevant results, the method of this aspect of the invention preferably includes imparting the amount of kinetic energy to a plurality of discrete particles and analysing resultant broken pieces of the particles following impact.

Thus the method preferably involves feeding discrete particles to be broken in turn into a guide channel and imparting a specific and consistent amount of kinetic energy to the particles. The particles are impacted against an impact surface at the predetermined impact velocity and the size distribution of the broken pieces of the particles analysed to determine breakage properties of the particulate material. This information can then be used to understand and model comminution processes in mills and the like.

The step of feeding particles in turn into the guide channel may comprise feeding particles through a feed channel and then into the guide channel.

The guide channel may be located in a rotor, for example as described in respect of the apparatus according to the earlier described aspect of the invention. If so, the step of displacing the particles along the guide channel may include rotating the rotor at a carefully controlled and/or measured speed and allowing the centrifugal force of the rotating rotor to impart the kinetic energy to the particles. The particles are projected from the rotor at a speed that is proportional to the speed of the rotor, and particularly the velocity of the circumferential edge of the rotor. Thus, a predetermined specific amount of kinetic energy can be imparted to the particle.

The step of causing the particle to impact with an impact surface may comprise causing the particle to strike the impact surface at an angle that is close to perpendicular with the impact surface.

Without being limited, the particles may be projected such that they strike the impact surface at an angle of 75 to 98 degrees to the surface, for example at 85 to 95 degrees to the surface, or substantially perpendicular to the surface.

The step of causing the particle to impact with an impact surface may alternatively comprise causing the particle to strike the impact surface with a glancing blow. As discussed above, with such a glancing blow the particle retains some kinetic energy and not all the energy is absorbed by the impact.

The glancing blow may be caused by orienting and/or configuring the impact surface differently to that for the perpendicular test described above.

The step of analysing the broken pieces of particle may include classifying the broken pieces from the collision into different size fractions, preferably automatically.

The broken pieces may be classified into two size fractions.

The step of classifying the broken pieces may comprise passing the pieces through a screen to divide the pieces up into oversize and undersize particles. The screen may for example have mesh openings that are approximately 1/10th of the mean size or diameter of the feed particles. This is known as the $T_{10}$ product fineness test that is used to calculate a product fineness index. As noted above, the product fineness index may be defined as the percentage of the mass of the initial feed material constituted by the percentage of the undersize material.

Further, the broken pieces may be classified into more than two size fractions, for example four to six size fractions.

The step of reviewing the broken pieces may also include weighing the broken pieces in each of the size fractions into which the pieces have been classified, preferably automatically.

The method may include repeating the steps set out above for a plurality of particles of the same general size or same size fraction to build up a particle size distribution of the broken pieces. This then provides an insight into how the particles of that size fraction break for a given input energy.

For example, a plurality of particles in one size range may be fed into a guide channel and then be caused to impact with the impact surface. At least 35 particles in one size range may be tested, for example 35-100 particles in one size range, for example 40-70 particles in each size range.

The particle breakage of a sample of 35-100 particles, for example about 50 particles can then be statistically analysed to build up a profile of how these particles will break. Preferably each particle size is tested at least three energy levels, for example at four to six energy levels, for example at four energy levels.

What has been described above is the method used to test one size fraction. The method may include pre-sizing the particles to be tested into narrow size fractions and then testing at least two or three different size fractions in turn in the manner set out above. A model of breakage distribution across the full spectrum of particles sizes in the feed can then be built up using curve fitting techniques.

Thus the process of testing a large sample of particles in each size fraction can be carried out. This way a particle size distribution of broken particles can be progressively built up for each of the size fractions into which the feed is pre sized.

The method may include testing particles that are mineral ore particles, for example from a crusher or from run of mine. The method may be used for all types of ores. The method may also be used on coal particles before the coal particles are sent to a coal grinding plant.

This invention also extends to a method of determining the breakage properties of particles on site at a commercial scale mill, for example online, using the apparatus or method described above.

The sample quantities of particulate material may be drawn from the feed to a commercial mill forming part of a commercial scale plant. The particulate material may be drawn off the feed stream to the mill on a regular basis and then subjected to testing in the apparatus, or by the method, in the manner described above.

The sample quantities of material are preferably drawn off the feed at least on a weekly basis, more preferably at least every three days, for example on a daily basis.

Thus, the apparatus may advantageously be placed in proximity to a commercial scale plant and the material tested from the feed stream to the mill in the apparatus.

Information on the breakage properties of the particulate material or breakage characterisation of the material may be given to plant managers and plant operators on a regular basis, for example on a daily basis.

It is envisaged that the above method may also be ideally placed to quantify the probability of breakage of the particulate material. That is, at very low and repetitive impacts, it may be possible to determine when particle of a particulate material will break substantially. This knowledge is emerging as a must-have in DEM modelling of mills and the future optimization of the process. To achieve statistically valid results, it is thought that the number of particles, required would be at least 200 for unconditioned particles, compared to say 30 or 50 for the t10 analysis described above. It may be possible to minimize that number to 50 particles, or slightly more, if the particles are first conditioned in a very low energy tumbling mill that essentially eliminates any abnormally weak particles and abrades away the surface asperities.

Accordingly, the method may include one in which the breakage property determined is the probability of breakage of the particulate material. In that case, the particles of the particulate material are preferably subjected to low energy milling to substantially eliminate abnormally weak particles of the particulate material prior to imparting kinetic energy to the particles. Also, at least 50 particles of the same general size or same size fraction of the pre-treated particles are tested.

DETAILED DESCRIPTION OF THE INVENTION

An apparatus and method for determining the breakage properties of particles in accordance with this invention may manifest itself in a variety of forms. It will be convenient to hereinafter provide a detailed description of one embodiment of the invention with reference to the accompanying drawings. The purpose of providing this detailed description is to instruct persons having an interest in the subject matter of the invention how to put the invention into practice. It is to be clearly understood however that the specific nature of this detailed description does not supersede the generality of the preceding statements. In the drawings:

FIG. 1 illustrates an apparatus that is used in the so called drop weight test that has been developed by and used by the Julius Kruttschnift Mineral Research Centre (JKMRC). FIG. 2 illustrates a similar apparatus using similar principles.

Figure 1:
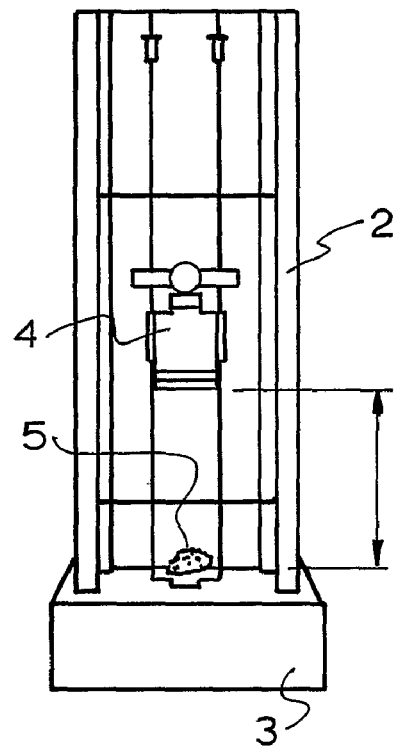
FIG. 1 is a schematic front view of an apparatus for characterising rock breakage that is known in the prior art.
Figure 2:
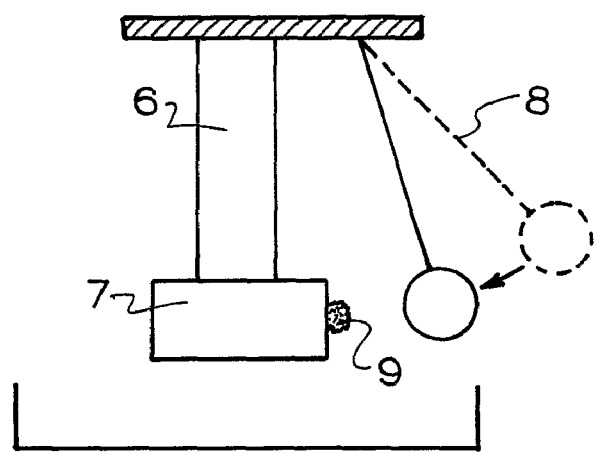
FIG. 2 is a schematic side view of another prior art apparatus similar to that in FIG. 1 showing how the apparatus impacts the test particle to cause breakage thereof.

The apparatuses in FIGS. 1 and 2 are discussed in the background to the invention above and will not be described further in this detailed description.

Figure 3:
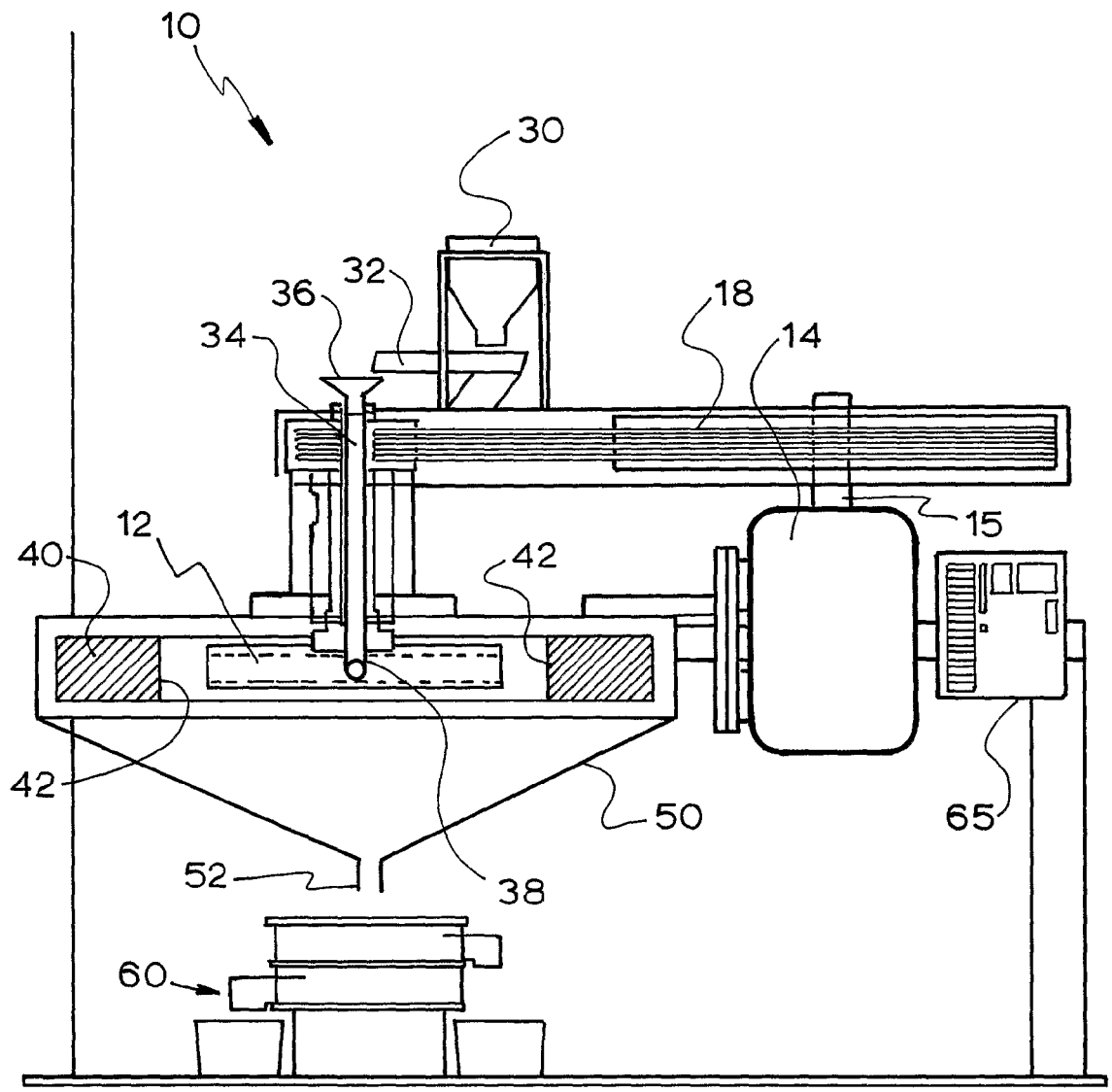
FIG. 3 is a schematic sectional front view of an apparatus in accordance with one embodiment of the invention.
Figure 4:
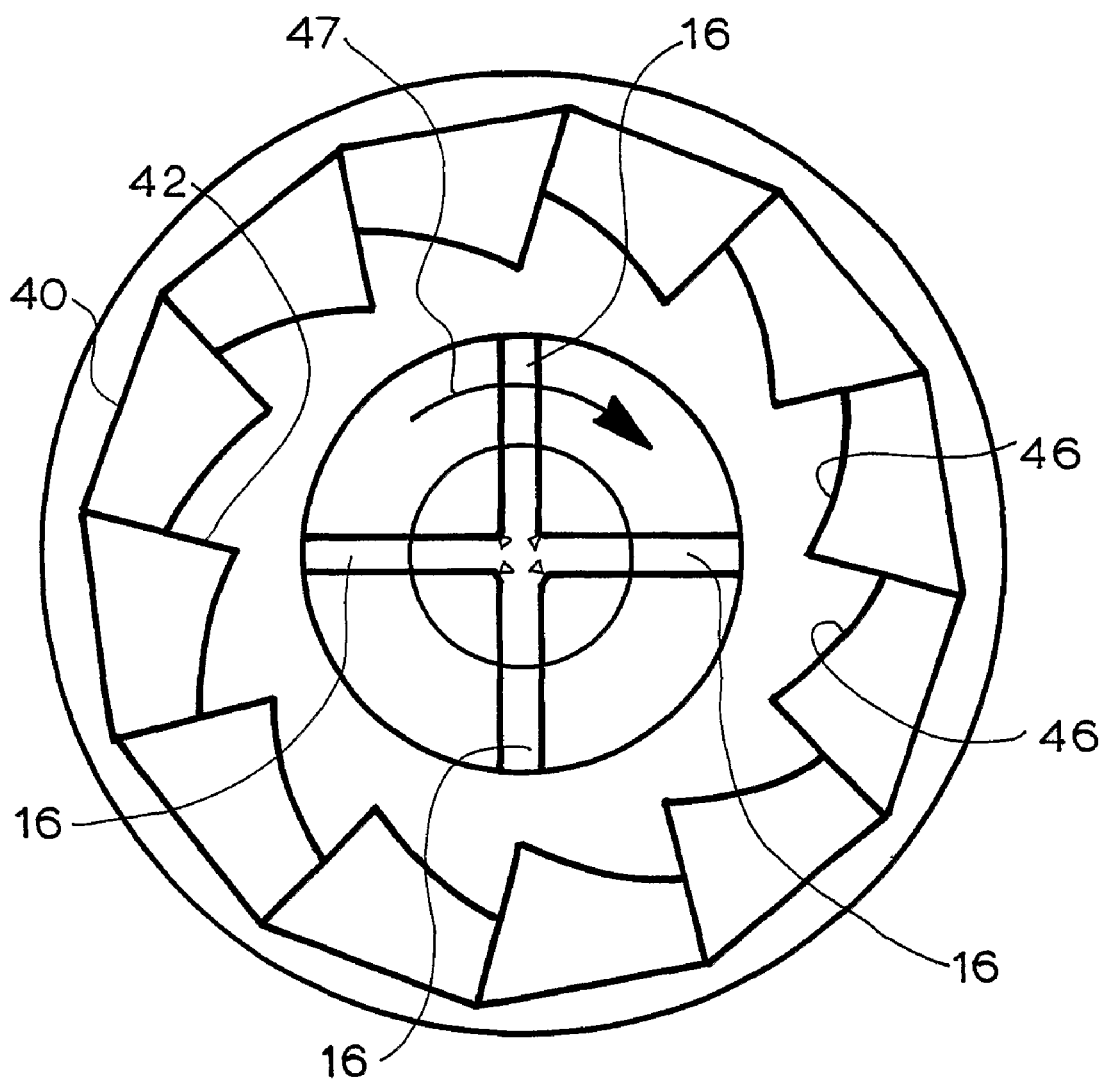
FIG. 4 is a schematic plan view of the apparatus of FIG. 3.
Figure 5:
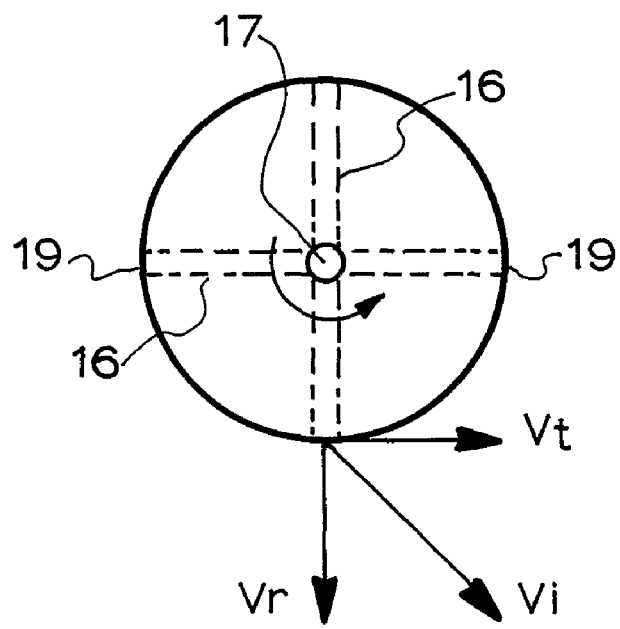
FIG. 5 is a schematic plan view of a rotor showing the component and resultant velocity vectors for a particle projected from the rotor.

In FIGS. 3 to 5 reference numeral 10 refers generally to an apparatus for characterising rock breakage properties in accordance with an embodiment of the invention.

The apparatus 10 comprises broadly a rotor that is shown generally by numeral 12 and a means for rotating the rotor in the form of an electric motor 14 having an output shaft 15.

The rotor 12 has a flat circular shape and has a plurality of guide channels 16 extending radially outward from its centre. In the illustrated embodiment there are four guide channels 16 that are spaced ninety degrees apart from each other although a precise number of guide channels 16 is not essential. The four guide channels 16 all merge into one in the centre of the rotor 12.

The guide channels 16 have a common inlet 17 at the point where they converge into one in the centre of the rotor 12. Particles to be tested are fed in through the inlet 17, defined by an open top of the guide channels 16 at this point. Further, each guide channel 16 has an outlet 19 on the circumferential edge of the rotor 12.

Figure 7:
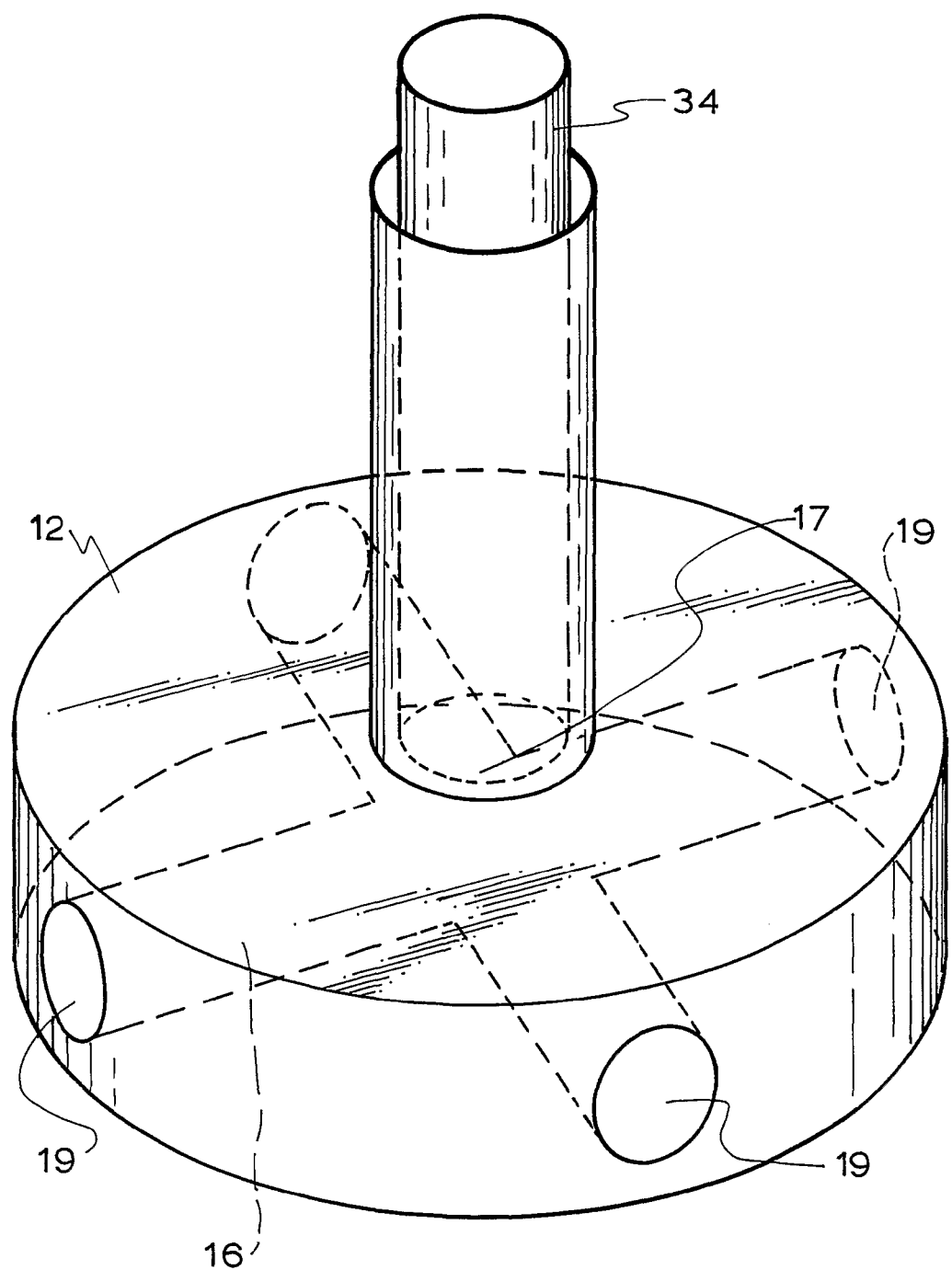
FIG. 7 is a three dimensional view of a rotor for the apparatus of FIG. 3 showing the channels through which the particles are passed.

In one form the rotor 12 is in the form of a block of steel and the guide channels 16 are milled or machined into the block. Such an example rotor is shown schematically in FIG. 7. In another form (not shown) the guide channels 16 comprise sections of pipe that are fixed onto an upper surface of the rotor 12.

The apparatus 10 also includes a drive transmission for transmitting drive from the motor 14 to the rotor 12. The drive transmission comprises a belt drive 18 extending between the motor 14 and the rotor 12. More specifically the belt drive 18 comprises three belt elements extending between pulleys associated with respectively the motor 14 and the rotor 12, the pulleys in turn being mounted on shafts extending from respectively the motor 14 and the rotor 12.

In the embodiment illustrated the motor 14 has a maximum speed of 1540 rpm that converts into a rotor speed of up to 5005 rpm by the pulley ratio of 3.25:1. Further the guide channels 16 define passageways in the rotor 12 of 30 mm diameter. The apparatus is advantageously capable of treating particles in a size range of 1 to 16 mm diameter. The apparatus can be modified to treat particles up to 100 mm in diameter and also small particle of less than 1 mm diameter.

The apparatus 10 also includes a control system for controlling the speed of the rotor 12. This controller comprises a variable frequency inverter (not shown) supplying current to the motor 14. Thus by varying the current supplied to the coil the speed of the motor 14 and thereby the speed of the rotor 12 can be varied.

The apparatus 10 also includes feed channel 34 for feeding particles in sequence into a the guide channels 16 of the rotor 12. The feed channel 34 is associated with a storage hopper 30 for storing a supply of particles from a given size fraction and a vibrating feeder 32 for displacing particles out of the storage hopper 30. The feed channel 34 has a substantially vertical orientation with an upper inlet 36 and a lower outlet 38.

The vibratory feeder 32 feeds particles from the hopper 30 one at a time into the inlet 36 of the feed channel 34.

The feed channel 34 has a diameter of about 30 mm and particles are passed in turn or in sequence through the feed channel 34. As a result only one particle issues from the outlet 38 of the feed channel 34 at a time. The outlet 38 of the feed channel 34 is positioned just above the rotor 12 such that particles are fed from the outlet 38 of the feed channel into the common inlet 17 of the guide channels 16.

The apparatus 10 also includes a stator 40 defining an impact surface 42 against which the particles collide after they fly out of an outlet 19 of a guide channel 16 on the circumferential edge of the rotor 10.

The stator 40 circumferentially surrounds the rotor 12 and has an inner surface defining the impact surface 42 that is spaced a short distance outwardly from the rotor 12. Naturally, the stator 40 will be positioned at substantially the same height as the rotor 12 so that particles flying off the rotor 12 strike it.

The impact surface 42 of the stator 40 may comprise curved segments or sections 46 that are arranged stepwise relative to each other as shown in FIG. 4. The stator 40 and impact surface 42 may be described as having a saw tooth shape when viewed in plan view.

Each curved segment 46 curves gradually in towards the edge of the rotor 12 in a direction that corresponds to the direction of rotation of the rotor 12 as shown by arrow 47 in the drawings.

The apparatus 10 further includes a collection chute 50 positioned beneath the stator 40 and rotor 12. The chute 50 has a conical shape and tapers inward in a downward direction to a chute outlet 52 at its lower end.

The apparatus 10 further includes means for analysing particles that have passed into the collection chute 50. The means for analysing the particles in the illustrated embodiment comprises a particle size classification apparatus 60. In the illustrated embodiment the classification apparatus 60 has a screen (not shown) and diverts oversize particles into an oversize fraction and undersize particles into an undersize fraction.

These relative fractions can then be weighed to see what fraction of the input feed particle weight they comprise. Their particle size distributions (PSD's) can also be determined.

In particular the product fineness index can then be calculated based on the initial mass of particles subjected to breakage and then the percentage of undersize material recovered from the classification apparatus 60.

The apparatus 10 also includes means for measuring the speed of the rotor. It is very important to get an accurate measure of the speed of the rotor as this forms the basis of the calculation of the input kinetic energy of the particles. In the illustrated embodiment the speed of the rotor 12 is measured by a tachometer (not shown). The speed sensor uses an inductive proximity sensor to detect the passing of a piece of steel (actually a bolthead) within 4 mm thereof each revolution. The sensor includes a coil and a magnet so that the flux through the coil will change as magnetic material passes it. The sensor feeds this information into a programmable counter that displays the rpm.

Further the apparatus 10 also includes controls for controlling the rate of feed of particles from the hopper 30 into the feed channel 34. It also includes a control for controlling a vibrating screen of the classification apparatus 60 positioned below the rotor and the collection chute.

Many of these controls are controlled from a control panel 65 that is positioned adjacent the electric motor 12. Further the control panel 65 may also include displays of one or more readings or measurements such as the speed of the rotor 12.

In use the apparatus 10 is typically used to characterise the breakage properties of particles from a certain ore body or a certain body of coal. These breakage properties can then be used to model or control or adjust unit operations that involve breakage of such particles such as comminution including milling.

In another embodiment that has not been illustrated the rotor 12 and stator 40 at least are fully enclosed in a vacuum chamber. This removes the effects of air resistance on the particles. This then assists in conducting tests to characterise the breakage of small particles.

The first step in a method to characterise ore particles would be to provide a sample of said ore particles covering a wide range of particle sizes and then to pre-size these particles into narrow fractions. This is typically done using a series of screens although it need not be done this way.

Thereafter each of the size fractions will be tested in turn in the apparatus 10. Typically this might be done by starting with the smallest size fraction and then working progressively through the different size fractions up to the biggest size fraction.

The first size fraction is charged into the feed hopper 30. The vibrating feeder 32 is then switched on and this jogs particles from the hopper 30 into the inlet 36 of the feed channel 34. The feed channel 34 is sized such that the particles arrange themselves in line or in a line sequence within the feed channel 34. This line of particles is then progressively displaced down the feed channel 34 towards the outlet 38.

Each particle issues from the outlet 38 in turn and drops through the common inlet 17 for the guide channels 16 in the centre of the rotor 12. From there the particles are urged to move in a radially outward direction by the centrifugal force of rotation of the rotor 12 along one of the guide channels 16. The guide channel 16 that the particle is displaced along will depend on the direction of centrifugal force that is applied to the particle at that particular time.

Each particle flies off, or out of the rotor 12 through the outlet 19 of the guide channel 16 at an angle to the rotor 12. The particle flies through the air and then collides with the impact surface 42 defined by the stator 40 that is in its path. Impact is at a specific predetermined impact velocity.

The impact surface 42 of the stator 40, with its saw tooth configuration as described above, ensures that each particle is moving in a direction substantially perpendicular to the impact surface segment 46 that it collides with. This feature helps to ensure that most of the kinetic energy in the particle is converted into breakage energy.

After colliding with the impact surface 42 the particle may break into a number of smaller pieces and these pieces then drop down through the collection chute 50 to its outlet 52.

The broken pieces then enter the classification apparatus 60 and depending on their size end up in undersize or oversize fractions.

This basic experiment is then repeated for a number of different particles, e.g. a large number of particles, in that size fraction. This way over time a statistically reasonable particle size distribution of the broken particles can be built up. This then shows how this particle will break up when subjected to this level of breakage energy.

This overall procedure is then repeated for a number of different energy levels to test the breakage of that particle size at the different energy levels. Different energy levels are imparted to the test particles by changing the speed of rotation of the rotor. By increasing the speed of the rotor greater kinetic energy is imparted to the particle when it flies off the rotor. This is then converted into greater collision energy when it collides with the impact formation. Very often the particle breakage characteristics are different for different energy levels. As such, it will be appreciated that the impact velocity, which is directly related to the energy level imparted to the particulate material, will be of considerable importance when determining breakage properties of the particulate material.

This procedure can be repeated for a plurality of the different narrow fractions into which the feed particles were divided, for example 3 to 4 fractions. This way a model of particle breakage for the different sizes can be progressively built up.

Applicant believes that it is likely that it will not be necessary to conduct the tests for all size fractions. Applicant believes that three to four size fractions may need to be tested to give an idea of the breakage characteristics over the whole size range.

FIG. 5 shows an example of the velocity vectors of a particle as it flies off the rotor.

The particles fly off the rotor with a radial velocity that has a tangential component vector and also a radial component vector. The actual path taken by this particle is the net resultant sum vector of these component vectors as shown in FIG. 5.

Applicant has conducted some investigation into and measurement of particle velocity using high speed video camera measurements. Applicant's investigations found that the particle radial velocity was less than the rotor circumference velocity. Applicant has established that the radial velocity of the particle flying off the rotor is not equal to the circumferential speed of the rotor. It is less than the speed of the circumference of the rotor. As a result Applicant has concluded that the final impact velocity is not equal to the square root of two times the circumferential velocity as per theory. However, Applicant has found that there is a linear relationship between the circumferential velocity and the particle velocity. That is, the impact velocity is proportional to the circumferential velocity. In particular, the two differ by a constant and one can be converted to the other.

The specific energy of each impact, Ecs, is defined as the kinetic energy $E_k$ per particle mass m:

$$Ecs = \frac{E_k}{m} \quad (1)$$
$$= \frac{0.5 \times m \times V_i^2}{m}$$
$$= 0.5 \times V_i^2$$

Hence the particle mass does not affect the specific energy in this type of impact breakage device. The specific energy is therefore dependent solely on the impact velocity $V_i$.

FIG. 5 shows that the impact velocity $V_i$ is resulted from the rotor tangential velocity $V_t$ and the radial velocity $V_r$, where:

$$V_i^2 = V_t^2 + V_r^2 \quad (2)$$

If the two velocity components are equal, $$V_i = \sqrt{2} \times V_t \quad (3)$$

If the two velocity components are not equal, $$V_i = C \times V_t \quad (4)$$

Therefore the specific energy is determined from $$Ecs = \frac{0.5 \times \left[C\left(\frac{2 \times \pi \times N \times r}{60}\right)\right]^2}{3600} \quad (5)$$

where Ecs is the specific energy (kWh/t), r the rotor radius (m), N the rotor speed (rpm), and C a machine design constant that governs the maximum possible impact velocity at a given rotor speed. This constant is believed to take into account the efficiency of a given design in transferring the kinetic energy from the rotor to the particle fed into the machine.

Figure 6:
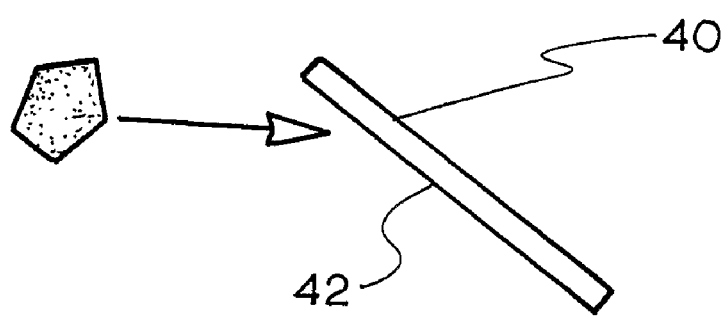
FIG. 6 is a schematic plan view of a particle and stator defining an impact surface for a low impact oblique collision.

FIG. 6 illustrates an impact surface in accordance with another embodiment of the invention.

As is shown in the FIG. 6 the impact surface 42 of the stator is arranged so that the particles collide with each of the impact surface segments at an oblique angle. This is quite different to the impact surface orientation described above with reference to FIG. 3 where the particle strikes the impact surface at substantially ninety degrees.

In use this formation is used to conduct shearing tests, which mimic the low energy breakage mode of attrition/abrasion in a mill. Narrowly sized particles are fed to the apparatus, impacted at the desired specific energy, and the product is screened and weighed. The oversize particles are subjected to another cycle of impact. The procedure is repeated until all particles are broken.

The apparatus developed by the Applicant in FIG. 3 together with the impact surface in FIG. 6 that is oriented to cause the particles to collide with the surface at an oblique angle provides a convenient and suitable means to conduct incremental breakage tests on the particles.

An advantage of the apparatus described above with reference to FIGS. 3 and 4 is that it operates largely automatically. That is, once particles have been fed into the hopper then the apparatus will feed individual particles one at a time into the feed channel and then onto the rotor. Further, the collecting chute and size classification system will recover the various size fractions automatically. Thus the operation of the system does not require active operator or technician involvement.

Further the apparatus could conduct a large number of tests of individual particles in a relatively short space of time. For example individual particles could be sent down the feed channel and onto the rotor every 1 second or so. That would enable 60 particles to be tested every minute and 120 particles to be tested every 2 minutes. This would enable test results that are obtained from the test work to be based on larger statistical samples and therefore be more accurate.

Another yet further advantage of the apparatus is that it can test size fractions of particles less than 10 mm diameter as easily as particles that are larger than 10 mm diameter. This is a significant advantage over the prior art apparatuses as Applicant believes small particles have different breakage properties to large particles.

Another advantage of the apparatus is that it is able to characterise breakage of both high energy impact at 90-degree and also low energy attrition/abrasion properties of ore particles. This is useful because both types of breakage occur in a working mill.

A yet further advantage of the apparatus described above is that it would be quite practical to have an apparatus permanently on site at a beneficiation plant and even possibly on line with the material streams to the mill. The testing of particle breakage properties could then be incorporated into the daily quality control and testing procedures of running the plant. In view of the fact that the apparatus runs largely automatically one it is set up for a particular size fraction existing operators could run this testing along with their existing duties. This instant almost real time information on particle breakage properties of particles going through the mill would enable plant engineers to respond to subtle changes in the breakage properties in the settings used for the mill.

Applicant believes that this invention has the potential to revolutionise operation of mills and the like. Historically mills have been very inefficient at converting input energy into particle breakage and this invention has the potential to significantly improve this.

It will of course be realised that the above has been given only by way of illustrative example of the invention and that all such modifications and variations thereto as would be apparent to persons skilled in the art are deemed to fall within the broad scope and ambit of the invention as herein set forth.

The invention claimed is:

1. An apparatus for determining the breakage properties of a particulate material, the apparatus including:
   a support;
   a rotor mounted relative to the support and including at least one guide channel through which a particle of the particulate material is guided in use, the guide channel having an inlet and an outlet;
   a drive associated with the rotor;
   a feed channel for feeding particles of the particulate material to the inlet of the guide channel;
   a stator associated with the rotor and including an impact surface that is radially spaced from a circumferential edge of the rotor; and
   a collector for collecting pieces of the particulate material following impact;
   wherein the apparatus is provided with a control system for accurate control and adjustment of impact velocity of the particulate material with the impact surface; and
   wherein the control system includes a processing unit for receiving an input of the circumferential speed of the rotor and correlating this with the actual impact velocity of a particle emitted from the guide channel of the rotor.

2. An apparatus according to claim 1, wherein the support includes a base for mounting or positioning the apparatus on a support surface and a frame extending up from the base.

3. An apparatus according to claim 2, wherein the frame includes upright members extending up from the base on at least two opposed sides of the base.

4. An apparatus according to claim 1, wherein the rotor includes a flattened, substantially circular body having two major surfaces.

5. An apparatus according to claim 4, wherein the rotor is oriented with its major surfaces extending in a substantially horizontal plane and the rotor rotates about a substantially vertical axis.

6. An apparatus according to claim 4, wherein the rotor is a solid, flat mass and the guide channel is defined by a channel that extends radially within the solid mass from a substantially central position to the circumferential edge of the rotor.

7. An apparatus according to claim 4, the inlet of the guide channel is formed by an opening in one of the major surfaces of the rotor, the opening being associated with the channel.

8. An apparatus according to claim 7, wherein the inlet is at or proximate to the central position of the rotor.

9. An apparatus according to claim 4, wherein the rotor includes a plurality of guide channels.

10. An apparatus according to claim 9, wherein the channels are circumferentially spaced from each other.

11. An apparatus according to claim 10, wherein the rotor includes four channels that have a common inlet positioned in the centre of the rotor and that extend substantially perpendicularly to each other.

12. An apparatus according to claim 11, wherein each channel extends linearly from the centre of the rotor to an outlet positioned on the circumferential edge of the rotor.

13. An apparatus according to claim 10, wherein the channels are equidistantly circumferentially spaced from each other.

14. An apparatus according to claim 1, wherein the drive includes an electric motor and a drive transmission that is coupled to the motor and the rotor to transmit drive from the motor to the rotor.

15. An apparatus according to claim 1, wherein the rotor is mounted on the support, a bearing being interposed between an upper formation associated with the rotor and a lower formation associated with the support.

16. An apparatus according to claim 1, wherein the control system controls the impact velocity of the particulate material within a difference of less than 2% relative to the circumferential speed of the rotor.

17. An apparatus according to claim 1, wherein the control system provides a means for finely adjusting the rotational speed of the rotor.

18. An apparatus according to claim 17, wherein the drive includes an electric motor and a variable frequency inverter is included to facilitate adjustment of the amount of current supplied to the motor correlating with adjustment of the rotational speed of the rotor.

19. An apparatus according to claim 17, including a potentiometer to facilitate adjustment of rotational speed of the rotor.

20. An apparatus according to claim 1, wherein the control system includes means for measuring the speed of rotation of the rotor.

21. An apparatus according to claim 20, wherein the control system includes an optical or mechanical tachometer.

22. An apparatus according to claim 1, wherein the feed channel extends substantially vertically and includes an inlet at an upper end and an outlet end at a lower end.

23. An apparatus according to claim 22, wherein the outlet of the feed channel is spaced above a common inlet to a plurality of guide channels of the rotor, substantially at the centre of the rotor.

24. An apparatus according to claim 22, wherein the feed channel includes a flared inlet for facilitating feeding of particles through the inlet.

25. An apparatus according to claim 1, wherein the feed channel is associated with a particle storage device that is positioned above the inlet to the feed channel, containing a supply of particles to be tested.

26. An apparatus according to claim 25, wherein the particle storage device has an outlet that is sized to limit the flow of particles through the outlet.

27. An apparatus according to claim 26, wherein the feed channel is associated with an intermediate conveying device for conveying particles from the outlet of the particle storage device to the inlet of the feed channel.

28. An apparatus according to claim 27, wherein the intermediate conveying device is a vibrating conveyor belt.

29. An apparatus according to claim 1, wherein the stator defining the impact surface includes a body that extends circumferentially around the rotor and that is spaced outwardly from the circumferential edge thereof.

30. An apparatus according to claim 29, wherein the impact surface is configured such that particles discharged from the guide channels of the rotor impact it at an angle of 70 degrees to 100 degrees.

31. An apparatus according to claim 30, wherein the impact surface includes a plurality of discrete surface segments arranged stepwise relative to each other extending around the impact surface.

32. An apparatus according to claim 31, wherein each of the surface segments is curved so that particles emitted from the rotor strike the impact surface at about ninety degrees.

33. An apparatus according to claim 31, wherein the stator includes a lining providing a wear surface that assumes wear resulting from the impact of particles discharging from the rotor.

34. An apparatus according to claim 33, wherein the lining includes a plurality of removable wear plates that can be removably attached to the stator and which can be removed and replaced with fresh wear plates as and when required.

35. An apparatus according to claim 1, wherein the stator is included in a lid adapted to enclose the rotor.

36. An apparatus according to claim 35, wherein the lid is mechanized.

37. An apparatus according to claim 1, including a housing within which the rotor and the stator are housed.

38. An apparatus according to claim 37, wherein the housing is sealed so that the air pressure within the housing can be reduced to below atmospheric pressure.

39. An apparatus according to claim 1, wherein the collector for collecting broken particles after impact includes a collection chute positioned beneath the rotor and stator.

40. An apparatus according to claim 1, including a classifier for classifying broken particles into different size groups.

41. An apparatus according to claim 40, wherein the classifier includes a plurality of classification screens, or includes an optical classifier.

42. An apparatus according to claim 40, wherein the collector includes means for weighing different size fractions of broken particles.

43. A method of determining breakage properties of a particulate material including the steps of:
feeding a plurality of discrete particles of the particulate material to the apparatus in accordance with claim 1;
analysing resultant broken pieces of the discrete particles following impact in the apparatus; and
correlating the resultant broken pieces with breakage properties of the particulate material.

44. The method according to claim 43, including dividing the particles of particulate material up into a plurality of size fractions and then testing each of the size fractions in turn in the apparatus of claim 1.

* * * * *